US006150345A

United States Patent [19]
Chun et al.

[11] Patent Number: 6,150,345
[45] Date of Patent: Nov. 21, 2000

[54] METHODS FOR PROMOTING SURVIVAL OF MYELIN PRODUCING CELLS

[75] Inventors: Jerold J. M. Chun; Joshua A. Weiner, both of La Jolla, Calif.

[73] Assignee: Regents of the University of California, Oakland, Calif.

[21] Appl. No.: 09/153,464

[22] Filed: Sep. 15, 1998

Related U.S. Application Data

[60] Provisional application No. 60/096,008, Aug. 10, 1998, and provisional application No. 60/096,924, Aug. 18, 1998.

[51] Int. Cl.$^7$ .............................. A61K 31/66; A61K 3/42; A61K 7/48; C07F 9/02
[52] U.S. Cl. ........................ 514/120; 514/785; 424/93.7; 435/325; 435/404; 558/86
[58] Field of Search ...................................... 514/120, 785; 424/93.7, 375; 435/325, 404, 240.2; 558/86

[56] References Cited

U.S. PATENT DOCUMENTS

| 5,521,223 | 5/1996 | Piazza et al. ............................ 514/785 |
| 5,565,439 | 10/1996 | Piazza et al. ............................ 514/110 |

OTHER PUBLICATIONS

Fukushima, N. et al. Proc. Natl. Acad. Sci. USA., vol. 95, 6151–6156.

Chun, J., "Lysophospholipid receptors: implications for neural signaling", *Critical Reviews in Neurobiology, Vol. 13, (2), XP000876903,* 151–168, (1999).

Weiner, J.A., et al. "Schwann cell survival mediated b the signaling phospholipid lysophosphatidic acid", *Pro. of the Nat'l Academy of Sciences of the USA, vol. 96 (9), XP002132110,* 52333–5238, (Apr. 27, 1999).

An et al., "Characterization of a Noval Subtype of Human G Protein–Coupled Receptor for Lysophosphatidic Acid," *J.Biol. Chem.,* 273:7906–7910 (1998).

An et al., "Molecular cloning of the Human Edg2 Protein and Its Identification as a Functional Cellular Receptor for Lysophospatidic Acid," *Biochemical and Biophysical Research Communications,* 231:619–622 (1997).

Blaschke et al., "Widespread programmed cell death in proliferative and postmitotic regions of the fetal cerebral cortex," *Development,* 122:1165–1174 (1996).

Blaschke et al., "Programmed Cell Death is a Universal Feature of Embryonic and Postnatal Neuroproliferative Regions Throughout the Central Nervous System, " *J. of Comparative Neurology,* 396:39–50 (1998).

Hawes et al., "Phospatidylinositol 3–Kinase Is an Early Intermediate In the Gβγ–Mediated Mitogen–activated Protein Kinase Signaling Pathway," *Journal of Biological Chemistry,* 271:12133–12136 (1996).

Hecht et al., "Ventricular Zone Gene–1 (vzg–1) Encodes a Lysophospatidic Acid Receptor Expressed in Neurogenic Regions of the Developing Cerebral Cortex," *J of Cell Biol.,* 135:1071–1083 (1996).

Lemke et al., "Identification and Purification of glial Growth Factor," *J. of Neuroscience,* 4:75–83 (1984).

Milano et al., "Enhanced Myocardial Function in Transgenic Mice Overexpressing the $\beta_2$–Adrenergic Receptor, " *Science,* 264:582–586 (1994).

Moolenaar et al., "Lysophospatidic acid: G–protein signaling and cellular responses," *Current Opinion in Cell Biology,* 9:168–173 (1997).

Syroid et al., "Cell Death in the schwann Cell Lineage and Its Regulation by Neuregulin," *Proc. Natl. Sci. USA,* 93:9229–9234 (1996).

Topilko et al., "Embryonic Development of Schwann Cells: Mulitple Roles for Neurequlins Along the Pathway," *Mol. Cell. Neurosci.* 8:71–75 (1996).

Vartaian et al., "A role for the acetylcholine receptor–inducing protein ARIA in oligodendrocyte development," *Proc. Natl. Acad. Sci. USA,* 91:11626–11630 (1994).

Weiner et al., "Lysophospatidic Acid Receptor Gene vzg–1/1pA1/edg–2 Is Expressed by Mature Oligodendrocytes During Myelination in the Postnatal Murine Brain," *Journal of Comparative Neurology,* 398:587–598 (1998).

Wyllie et al., "Chromatin Cleavage In Apoptosis: Association With Condensed Chromatin Morphology and Dependence on Macromolecular Synthesis"*J. of Pathology,* 142:67–77 (1984).

Zondag et al., "Sphingosine 1–phosphate signaling through the The G–Protein–coupled receptor Edg–1," 330:605–609 (1998).

An, et al., "Characterization of a Novel Subtype of Human G Protein–coupled Receptor for Lysophosphatidic Acid", *J. Biol. Chem.,* vol. 273, No. 14, 7906–7910, (Apr. 3, 1998).

Bandoh, et al., "Molecular Cloning and Characterization of a Novel Human G–protein–coupled Receptor, EDG7, for Lysophospatidic Acid", *The Journal of Biological Chemistry,* vol. 274, No. 39, 27776–27785, (Sep.24, 1999).

Chun, et al., "A Growing Family of Receptor Genes for Lysophosphatidic Acid (LPA) and other Lysophospholipids (LPs)", *Cell Biochemistry and Biophysics,* vol. 30, No. 2, 213–242, (1999).

Lee, et al., "Lyosphospatidic Acid Stimulates the G–protein–coupled Receptor EDG–1 as a Low Affinity Agonist", *The Journal of Biological Chemistry,* vol. 273, No. 34, 22105–22122, (Aug. 21, 1998).

*Primary Examiner*—M. Borin
*Attorney, Agent, or Firm*—Schwegman, Lundberg, Woessner & Kluth, P.A.

[57] ABSTRACT

The present invention provides a method for promoting the survival of myelin producing cells, in particular SCs and oligodendrocytes. Other embodiments of the present invention are directed to therapeutic methods, utilities, and other related uses.

16 Claims, 11 Drawing Sheets

METHODS FOR PROMOTING SURVIVAL OF MYELIN PRODUCING CELLS

This application claims the benefit of U.S. Provisional Application No. 60/096,008, filed Aug. 10, 1998, and U.S. Provisional Application No. 60/096,924, filed Aug. 18, 1998, and incorporated by reference.

FIELD OF THE INVENTION

This invention is in the field of neurobiology, and relates particularly to methods useful for enhancing the survival of myelin producing cells, in particular Schwann cells and oligodendrocytes, and thereby to treating diseases of the nervous system involving loss of myelination or aberrant myelination.

BACKGROUND OF THE INVENTION

Schwann cells (SCs) and oligodendrocytes are important glial cells that provide myelin sheathing around the axons of neurons. Schwann cells provide myelin sheathing around axons in the peripheral nervous system and oligodendrocytes provide myelin sheathing around axons in the central nervous system.

During peripheral nerve myelination in the early postnatal period, the matching of SC and axon numbers is regulated by SC apoptosis, resulting in the mature 1:1 relationship between axons and myelinating SCs. After this period of SC proliferation and myelination, SCs are generally inactive. However, upon injury SCs will demyelinate around the injured axon and reenter the cell cycle thereby remyelinating the regenerated axon. Accordingly, it is believed that SCs receive survival and differentiation signals from growing axons during peripheral nerve development and regeneration, based on studies of SCs following nerve transection. It has also been shown that oligodendrocytes will remyelinate after pathological lesions to the central nervous system.

Myelin producing cells thus play an important role in the development, function, and regeneration of nerves. The implications of this from a therapeutic perspective have been addressed by Levi et al. in J. Neurosci., 1994, 14(3):1309, where the authors discuss the potential for cellular prostheses comprising human SCs which could be transplanted into areas of damaged spinal cord. Accordingly, these authors outline the need for SC mitogens which can be used to allow full differentiation of these cells ex vivo. The published patent application, WO 94/00140, describes the use of various factors for stimulating mitogenesis of glial cells including SCs. Others have demonstrated that neuregulin is a potent mitogen for human SCs in vitro.

Agents that promote growth and survival of myelin producing cells can be useful for a variety of therapeutic purposes. Diseases and conditions of the nervous system that result from the deterioration of, or damage to, the myelin sheathing generated by myelin producing cells are numerous. Myelin may be lost as a primary event due to direct damage to the myelin or as a secondary event as a result of damage to axons and neurons. Primary events include neurodegenerative diseases such as Multiple Sclerosis, human immunodeficiency MS-associated myelopathy, transverse myelopathy/myelitis, progressive multi focal leukoencepholopathy, central pontine myelinolysis and lesions to the myelin sheathing (as described below for secondary events). Secondary events include a great variety of lesions to the axons or neurons caused by physical injury, ischemia diseases, malignant diseases, infectious diseases (such has HIV, Lyme disease, tuberculosis, syphilis, or herpes), degenerative diseases (such as Parkinson's, Alzheimer's, Huntington's, ALS, optic neuritis, postinfectious encephalomyelitis, adrenoleukodystrophy and adrenomyeloneuropathy), nutritional diseases/disorders (such as folic acid and Vitamin B12 deficiency, Wernicke disease), systemic diseases (such as diabetes, systemic lupus erthematosis, carcinoma), and toxic substances (such as alcohol, lead, ethidium bromide); and iatrogenic processes such as drug interactions, radiation treatment or neurosurgery.

Lysophosphatidic acid (LPA) is a bioactive lipid with properties of an extracellular growth factor for many cell lines. However, the relationship between LPA and complex tissues such as the developing nervous system has been unclear.

It has now been surprisingly found that agents that stimulate LPA receptors, such as LPA, have the desirable property of promoting the survival of myelin producing cells, in particular SCs and oligodendrocytes.

SUMMARY OF THE INVENTION

The present invention provides a method for promoting the survival of myelin producing cells, in particular SCs and oligodendrocytes. Other embodiments of the present invention are directed to therapeutic methods, utilities, and other related uses.

One aspect of the present invention is a method for promoting the survival of myelin producing cells comprising treating myelin producing cells with an effective amount of an LPA receptor agonist. In particular, there is provided a method for promoting the survival of Schwann cells comprising contacting Schwann cells with an effective amount of an $LP_{A1}$/VZG-l/edg-2 receptor agonist.

Another aspect of the present invention is a method for enhancing the development or regeneration of myelin by promoting the survival of myelin cells comprising treating myelin producing cells with an effective amount of an LPA receptor agonist. In a preferred embodiment, the myelin producing cells are Schwann cells and the LPA receptor agonist is an $LP_{A1}$/VZG-l/edg-2 receptor agonist.

Yet another aspect of the invention is a method for promoting survival of endogenous myelin producing cells in a subject, comprising delivering to the subject an effective amount of an LPA receptor agonist. In a particular embodiment, the myelin producing cells are SCs and the LPA receptor agonist is an $LP_{A1}$/VZG-l/edg-2 receptor agonist.

Another aspect of the invention is a pharmaceutical composition useful for treating a neurological disorder involving a loss of myelination comprising of an effective amount of an LPA receptor agonist, in particular, an effective amount of a $LP_{A1}$/VZG-l/edg-2 receptor agonist.

Another aspect of the invention is a method for treating a subject with a neurological disorder involving a loss of myelination comprising of delivering to the subject an effective amount of an LPA receptor agonist, in particular, an effective amount of a $LP_{A1}$/VZG-l/edg-2 receptor agonist.

Another aspect of the invention is a serum-free medium suitable for culturing myelin producing cells, (in particular, SCs) comprising of an effective amount of a LPA receptor agonist (in particular, a $LP_{A1}$/VZG-l/Edg 2) to promote survival of the myelin producing cells, and suitable cell culturing excipients necessary for cell viability.

BRIEF DESCRIPTION OF THE DRAWINGS

Embodiment s of the invention are described hereinafter with reference to the accompanying drawings as described below.

DEFINITIONS

Figure 1:
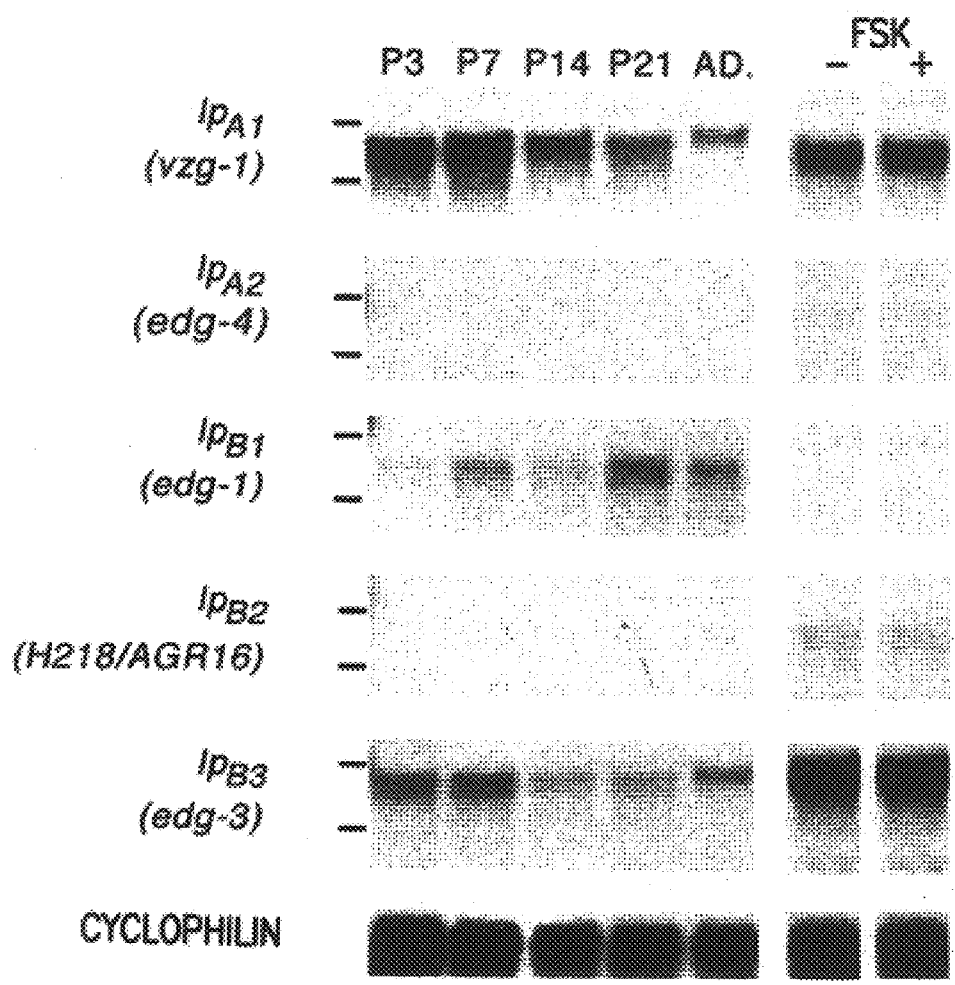
FIG. 1. Members of the lysphospholipid (lp) receptor gene family are expressed in SCs in vivo and in vitro. Northern blots of 10 μg total RNA from sciatic nerve (a) at various postnatal (P) ages to adult (AD.), or of 15 μg total RNA from cultured neonatal (P3) sciatic nerve SCs (b) grown with (+) and without (−) forskolin (FSK), were probed for transcripts encoding five members of the LP GPCR family [Chun, J., et al., *Cell Biochem. and Biophys.* in press (1998)]. The LPA receptor $lp_{A1}$/vzg-l is expressed at high levels by SCs both in vivo, especially in the first 2 postnatal weeks, and in vitro with and without FSK, which induces a more differentiated SC phenotype [Gould, et al., *Biol. and Chem.* (ed. Martenson, R. E.) 123–171 (CRC Press, Boca Raton, 1992)]. Expression of a related receptor gene ($lp_{A1}$/SCS -4) recently reported to mediate LPA responses [An, S., et al., *J. Biolog. Chem.* 273, 7906–7910 (1998)] was undetectable in SCs either in vivo or in vitro. Of 3 genes ($lp_{B1-3}$) which encode S1P receptors [Lee, et al., *Science* in press (1998)], only $lp_{B3}$ is prominently expressed by neonatal SCs in vitro, although both $lp_{B1}$ and $lp_{B3}$ are expressed at various ages in vivo (the absence of $lp_{B1}$ expression in vitro reflects the very low expression in the sciatic nerve at P3, the age at which cultures were made). A cyclophilin probing is shown as a loading and transfer control. Upper marker is 4.4 kb and lower marker is 2.4 kb in each panel.

In general, the following words or phrases have the following meanings:

"Administer" means the process by which the desired agent or progenitor of the agent, e.g., prodrug, is delivered to the subject, such that said agent is contacted with the organs, tissues or cells of the subject in need of treatment. Administration can be made by any accepted systemic or local route.

"Cell culturing excipients" are those excipients necessary for sustaining the viability of cells in a cell culture environment.

"Effective amount" means that amount of an active agent when administered to a subject in need thereof, is sufficient to bring about the desired effect. For example, in the present invention an effective amount is such amount when administered to a subject would promote survival of myelin producing cells, such as, SCs or oligodendrocytes.

"Ex vivo" means where cells are taken outside of a living organism to undergo a process or processing and then reintroduced back to a living organism.

"In vitro" means outside of a living organism; pertaining to conditions or to experiments with a perfused organ, a tissue slice, cells in tissue culture, a homogenate, a crude extract or a subcellular fraction.

"LPA receptors" are sites that LPA interact with, e.g., by binding, to manifest physiological or pathophysiological effects of LPA.

"LPA receptor agonists" are agents that interact with LPA receptors, including LPA and other agents, which are sufficiently structurally similar to LPA, such that they will also interact with the LPA receptor, e.g., other lysophospholipids. LPA receptor agonists can be determined by employing the assay set out in Hecht et al. *J. Cell Bio.* 135 1071-1083 (1996) (Reference 2), incorporated herein by reference, and which encompasses the use of $^3$H-LPA bound specifically to cells that overexpress or heterologously express the LPA receptor (see also Fukushima et al., *PNAS USA*, 95: 6151-6156, 1998, incorporated herein by reference). A single receptor encoded by vzg-1/lp$_{A1}$/edg 2 couples to G-proteins and mediates multiple cellular responses to LPA (Fukushima et al., supra.) Other assays include the use of cell rounding or stress fiber formation in cells that do not express the receptor; once the receptor is heterologously expressed, these cells will then either round (in the case of the neuroblastoma cell line B103) or form stress fibers (for the liver cell line RH7777 when exposed to LPA at nM concentrations but not after exposure to related ligands. Another assay is to measure cAMP levels, since LPA activating its receptor produces a decrease in cAMP by activation of the heterotrimeric G-protein G$_i$. Another way is to assay the proximal event in G-protein coupling through the use of 35S-GTPS labeling of G-proteins that is dependent of the presence of an LPA receptor and LPA stimulation. Each of these methods is standard and known to those skilled in the art, as noted in the citations.

"Myelin producing cells" are cells that provide myelin and myelin sheathing, typically around the axons of neurons, such as SCs and oligodendrocytes.

"Neurological disorder" is any disease, disorder, injury or iatrogenic process of, or in the nervous system that results from, or results in, deterioration, or damage to the myelin sheathing and/or non-myelinated parts of the myelin producing cells that affects the process, maintenance or normal turnover/metabolism involved in myelination by myelin producing cells, including but not limited to, neurodegenerative diseases of the myelin (such as, Multiple Sclerosis, human immunodeficiency MS-associated myelopathy, transverse myelopathy/myelitis, progressive multi focal leukoencephalopathy, central pontine myelinolysis); damage to the nervous system (such as lesions caused by physical injury); ischemia diseases; malignant diseases; infectious diseases (such as HIV, Lyme disease, tuberculosis, syphilis, or herpes); degenerative diseases (such as Parkinson's, Alzheimer's, Huntington's ALS, optic neuritis, postinfectious encephalomyelitis, adrenoleukodystrophy, and adrenomyeloneuropathy); nutritional diseases/disorders (such as folic acid and Vitamin B12 deficiency, Wernicke disease); systemic diseases (such as diabetes, systemic lupus erthermatosot, carcinoma); toxic substances (such as alcohol, lead ethidium bromide; and iatrogenic processes (such as drug interactions, radiation treatment or neurosurgery).

"Pharmaceutically acceptable excipients" refers to ingredients that are combined with an active agent to form a pharmaceutical composition. Typically pharmaceutically acceptable excipients include, but are not limited to, a conventional pharmaceutical carrier, other medicinal agents, pharmaceutical agents, carriers, adjuvants, etc. Carriers can be selected from the various oils, including those of petroleum, animal, vegetable or synthetic origin (e.g., peanut oil, soybean oil, mineral oil, sesame oil, and the like). Water, saline, aqueous dextrose, and glycols are preferred liquid carriers, particularly for injectable solutions. In addition, suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Preferably pharmaceutical compositions will take the form of a capsule, pill or tablet, and thus pharmaceutically acceptable excipients will include but are not limited to a diluent such as lactose, sucrose, dicalcium phosphate, and the like; a disintegrant such as starch or derivative thereof; a lubricant such as magnesium stearate and the like; and a binder such as a starch, polyvinylpyrrolidone, gum acacia, gelatin, cellulose and derivatives thereof, and the like. For oral administration to infants, a liquid formulation (such as a syrup or suspension) is preferred. Other suitable pharmaceutical carriers and their formulations are describe in "*Remington's Pharmaceutical Sciences*" by E. W. Martin.

"Promoting survival of myelin producing cells" means increasing the lifespan of myelin producing cells.

"Serum-free cell growth medium", "serum-free medium" or "serum-free composition" refers to compositions that are essentially free of serum from any mammalian source, e.g., where the composition contains less than about 5% serum, preferably less than about 1%, and most preferably between 0–0.1%.

"vzg-1" is a G-protein coupled receptor for LPA termed ventricular zone gene-1, alternatively this receptor is also designated lp$_{A1}$ or edg-2.

DETAILED DESCRIPTION OF THE INVENTION

The present invention is directed to LPA and related agonists of LPA receptors which regulates myelination by promoting survival of myelin producing cells. In particular, it is demonstrated that LPA and related agonists of the LPA receptors, including LP$_{A1}$/VZG-1/edg 2, have the potential to promote SC survival by activation of such LPA receptors. More particularly, it is shown that LPA is a potent, specific survival factor for neonatal SCs, with efficacy comparable to that of neuregulins. In view of the expression of the LP$_{A1}$/VZG-1/edg 2 receptor by oligodendrocytes [Weiner, J. A., et al., *J. Compar. Neuro.* 398, 587–598 (1998)] a similar biological response to LPA and agonists of LPA receptors, in particular agonists of LP$_{A1}$/VZG-1/edg 2 receptors, should be observed in oligodendrocytes during central nervous system myelination in development and following injury. Furthermore, by promoting the survival of myelin producing cells the regeneration and development of myelin will be enhanced by the virtue of the viability of such surviving myelin producing cells. Accordingly, LPA and other agonists of LPA receptors, in particular agonists of LP$_{A1}$/VZG-1/edg 2 receptors, have therapeutic utility to a range of disorders in which myelination is perturbed.

LPA is present in serum in the micromolar range [Eichholtz, et al., *Biochem. J.* 291, 677–680 (1993)], making it a candidate molecule for mediating the SC survival-promoting effects of serum. Furthermore, the LPA receptor gene lp$_{A1}$/vZg-1 [Hecht, et al., *J. Cell Bio.* 135, 1071–1083 (1996)] is well placed to mediate such effects since it is expressed by sciatic nerve SCs in vivo throughout the postnatal period, with highest expression in the first week (FIG. 1a). Similarly, lp$_{A1}$/vzg-1 is expressed at comparable levels by neonatal SCs in vitro (FIG. 1b). Other members of the recently identified lysophospholipid (LP) GPCR family, including identified receptors for the structurally and functionally related lipid sphingosine-1-phosphate (SlP) [Lee, et al., *Science* in press (1998); Chun, J., et al., *Cell Biochem. and Biophys.* in press (1998); An, S., et al., *J. Biolog. Chem.* 273, 7906–7910 (1998); Zondag, G. C. M., et al., *Biochem. J.* 330, 605–609 (1998)], are also expressed by SCs (FIG. 1). These data indicate the potential action of receptor-mediated lysophospholipid signaling pathways during SC maturation.

As exemplified below, LPA (10 nM) is a potent survival factor for cultured neonatal SCs, with survival activity equaling maximal effects of neuregulin, a demonstrated peptide survival factor [Dong et al., *Neuron* 15, 585–596 (1995), Syroid, et al., *PNAS USA* 93, 9229–34 (1996), Grinspan, et al., *J. Neurosci.* 16, 6107–18 (1996)]. It is demonstrated herein that LPA activates a pharmacologically defined signaling pathway in SCs, involving G$_1$ and phosphoinositide 3-kinase (P13K), and induces phosphorylation of Akt, a kinase that mediates P13K-dependent survival [Dudek, et al., *Science* 275, 661-665 (1997), Franke et al., *Cell* 88, 435–437 (1997)]. It is also demonstrated that overexpression of epitope-tagged LP$_{A1}$/VZG-1/edg 2 increased LPA-dependent SC survival. Accordingly, LPA is a factor in SC survival during myelination, and LPA receptors, particularly the LP$_{A1}$/VZG-1/Edg 2 receptor, are activated by LPA in its role in promoting SC survival.

Pharmaceutical Compositions

The pharmaceutical compositions of this invention are useful in promoting the survival of myelin producing cells, in particular, Schwann cells and oligodendrocytes. Therefore, these compositions are particularly useful for preventing, treating or ameliorating diseases and/or conditions of the nervous system that result from the deterioration of, or damage to, the myelin sheathing generated by myelin producing cells are numerous. Myelin may be lost as a primary event due to direct damage to the myelin or as a secondary event as a result of damage to axons and neurons. Primary events include neurodegenerative diseases such as Multiple Sclerosis, human immunodeficiency MS-associated myelopathy, transverse myelopathy/myelitis, progressive multi focal leukoencepholopathy, central pontine myelinolysis and lesions to the myelin sheathing (as described below for secondary events). Secondary events include a great variety of lesions to the axons or neurons caused by physical injury, ischemia diseases, malignant diseases, infectious diseases (such has HIV, Lyme disease, tuberculosis, syphilis, or herpes), degenerative diseases (such as Parkinson's, Alzheimer's, Huntington's, ALS, optic neuritis, postinfectious encephalomyelitis, adrenoleukodystrophy and adrenomyeloneuropathy), nutritional diseases/disorders (such as folic acid and Vitamin B12 deficiency, Wernicke disease), systemic diseases (such as diabetes, systemic lupus erthematosos, carcinoma), and toxic substances (such as alcohol, lead, ethidium bromide); and iatrogenic processes such as drug interactions, radiation treatment or neurosurgery.

Administration

The pharmaceutical composition of the present invention comprises an effective amount of a LPA receptor agonist, and pharmaceutically acceptable excipients. Those of ordinary skill in the art recognize that an "effective amount" means that amount of an active agent when administered to a subject in need thereof, is sufficient to bring about the desired effect. For example, in the present invention an effective amount is such amount when administered to a subject would promote survival of myelin producing cells, such as, SCs or oligodendrocytes. Administration of the active compounds and salts described herein can be via any of the accepted modes of administration for active agents that serve similar utilities.

The level of active agent in a formulation can vary within the full range employed by those skilled in the art, e.g., from about 0.01 percent weight (% w) to about 99.99% w of the drug based on the total formulation and about 0.01% w to 99.99% w excipient.

Generally, an acceptable daily dose is of about 0.001 to 50 mg per kilogram body weight of the recipient per day, preferably about 0.05 to 10 mg per kilogram body weight per day. Thus, for administration to a 70 kg person, the dosage range would be about 0.07 mg to 3.5 g per day, preferably about 3.5 mg to 1.75 g per day, and most preferably about 0.7 mg to 0.7 g per day depending upon the individuals and disease state being treated. Such use optimization is well within the ambit of those of ordinary skill in the art.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Liposomal Formulations

Pharmaceutical formulations based on liposomes have recently reached human clinical trials. Their benefits are believed related to favorable changes in tissue distribution and pharmacokinetic parameters that result from liposome entrapment of drugs. Those of ordinary skill in the art would recognize that the taught structure of the LPA receptor agonists of the present invention, i.e., LPA and other agents, which are sufficiently structurally similar to LPA, such that they will also interact with the LPA receptor, e.g., other lysophospholipids, could be advantageously formulated in a liposomal formulation.

EXAMPLES

The following examples are given to enable those skilled in the art to more clearly understand and to practice the present invention. They should not be considered as limiting the scope of the invention, but merely as being illustrative and representative thereof.

EXAMPLE 1

Preparation of Scs: Reagents and Pharmacological Treatmentss

Lyophilized LPA (1-Oleoyl-2-Hydroxy-sn-Glycero-3-Phosphate; Avanti Polar Lipids) was resuspended in 1% fatty acid-free (FAF) BSA (Sigma), and diluted for experiments in the same solution. Sphingosine-1-phosphate (S1P) (Biomol) was dissolved in methanol, aliquoted and lyophilized, and resuspended for experiments in 0.01% FAF BSA. S1P activity was confirmed in an independent morphological assay using the B103 neuroblastoma cell line [Fukushima, N., et al., *PNAS USA*. in press (1998)]. Wortmannin, LY294002, and PD98059 (Calbiochem) were dissolved in DMSO at 10 mM, 50 mM or 100 mM, respectively, and diluted in PBS for experiments. Pharmacological inhibitors were added at the time of serum withdrawal and LPA addition for ISEL+ experiments, or at the time of serum withdrawal and 2 hours before LPA treatment for Akt experiments. For ISEL+ experiments, pertussis toxin (Calbiochem) was added to cultures 18 h prior to serum withdrawal, at the time of serum withdrawal and LPA addition, and again 24 h later. Truncated GST-NRG (encompassing the EGF-like motif, see [Carraway, K. L., et al., Nature 387, 512–516 (1997)] for sequence) was the generous gift of Dr. Cary Lai, Scripps Research Institute, La Jolla, Calif.

Primary SC Culture

Sciatic nerves were excised from postnatal day 3 rat pups, and SCs purified essentially as previously described [Brockes, J. P., et al., Brain Res 165, 105–118 (1979)]. Cells were grown on poly-L-lysine (0.1 mg/ml) coated dishes, or on poly-L-lysine and laminin (10 μg/ml) coated 8-well plastic Chamber Slides (Nunc) and glass coverslips. Growth medium was DMEM (Gibco) supplemented with 10% FCS, 20 μg/ml pituitary extract (Sigma), 2 μM forskolin, and penicillin/streptomycin. SC cultures were >98% pure as assessed by anti-P* and anti-S100 (Dako) immunoflourescence. For proliferation experiments, cultures at 24 h post-serum withdrawal were pulsed for and additional 24 h with BrdU, and cells were fixed and processed for BrdU immunoflourescence (BrdU Labeling and Detection Kit, Boehringer Mannheim).

Northern Blot Analyses

Total RNA was isolated from mouse sciatic nerves at various ages, and from cultured rat SCs using Trizol reagent (Gibco). Northern blots of 7, 10, or 15 μg of RNA were made using standard protocols, and were probed with $^{32}$P-labeled open reading frame fragments of murine LP family receptor cDNAs at $5\times10^5$ cpm/ml.

ISEL+ Identification of Apoptotic Cells

SCs were grown to near-confluence on 8-well Chamber Slides. Media was changed to serum free DMEM, with or without LPA or other treatments as indicated. Cells were fixed in 4% paraformaldehyde 48 h later, and ISEL+ analyses were performed as previously described [Blaschke, A. J., et al., Development 122, 1165–1174 (1996); Blaschke, A. J., et al., J. Compar. Neuro. 396, 39–50 (1998)]. All experimental treatments were performed at least 3 times in duplicate and over 1000 cells were counted per well. For counts of cell number, nonapoptotic DAPI-labeled nuclei (those with a normal, oval morphology and absence of any ISEL+ labeling) were counted in 10 fields of view (at 400×) per well. Cell counts were performed on duplicate slide wells from at least 3 experiments per condition.

Akt Western Blot Analyses

SCs were grown to confluence in 6-well dishes and switched to DMEM/1% FCS for 24 h to reduce basal Akt phosphorylation. Media was changed to serum-free DMEM with or without pharmacological inhibitors, and 2 h later LPA (1 μM) was added. Media was removed at the indicated times and cell samples prepared, western blotted, and detected using the PhosphoPlus Ser473 Akt Antibody kit (New England Biolabs).

Transrection of SCs

SCs were grown on glass coverslips to approximately 80% confluency, and were transfected for 3 h using Lipofectamine Plus (Gibco) in DMEM/10% FCS (no antibiotic). pFLAG/VZG-1 [Fukushima, N., et al., PNAS USA in press (1998)] contains the complete open-reading frame of murine $lp_{A1}$/VZg-1 fused to an N-terminal FLAG epitope sequence in the plasmid pFLAG/CMV2 (Kodak/IBI). pFLAG/BAP control plasmid was obtained from Kodak/IBI. After transfection, cells were switched to growth medium for 12 h to allow for protein expression, and then switched to serum free DMEM with or without LPA for 24 h. Cells were fixed for 30 min with 4% paraformaldehyde, and sequentially processed for fluorescent ISEL according to manufacturer's instructions (Fluorescein in Situ Cell Death Kit, Boehringer Mannheim) and anti-FLAG immunofluorescence (anti-FLAG M2 monoclonal antibody, Kodak/IBI, 1:6000). Three separate experiments were performed in triplicate and all transfected cells on each coverslip were counted (~150–350 cells/coverslip). Baseline apoptosis due to transfection alone was assessed in parallel coverslips maintained in 10% FCS (in which untransfected cells exhibit <1% apoptosis), and this value was subtracted from each experimenta 1 value.

Example 2

LPA and Promotion of SC Survival

SCs exhibit little cell death (<1%) when cultured in standard growth medium containing fetal calf serum [FCS; data not shown, Syroid, D. E., et al., PNAS USA 93, 9229–34 (1996)]. However, apoptosis can be initiated in primary cultures of SCs by withdrawal of serum, which serum includes survival factors likely supplied by growing axons in vivo.

Figure 2A:
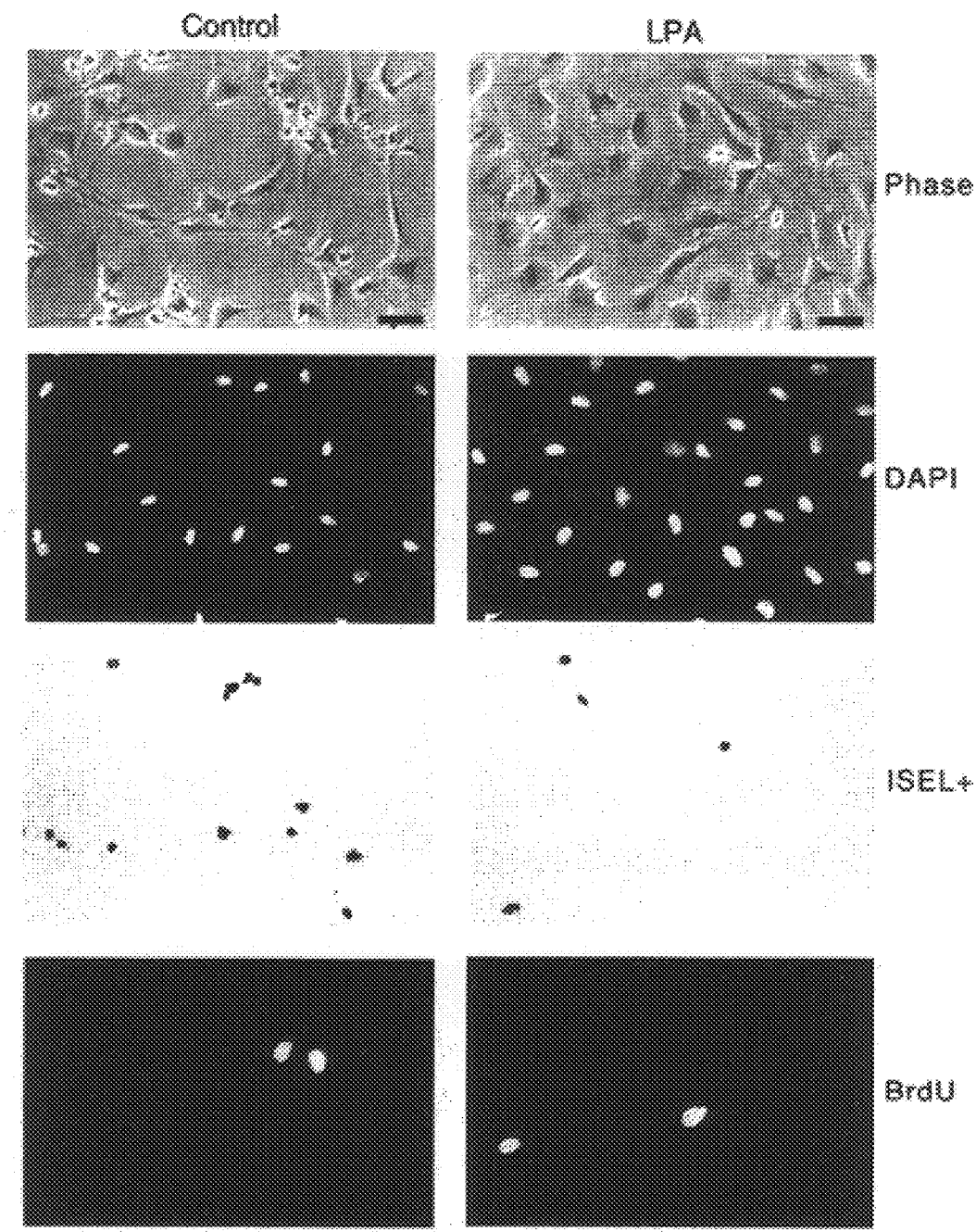
FIG. 2. LPA is a specific, potent survival factor for SCs following serum withdrawal. a) photomicrographs of control and LPA (1 μM) treated SC cultures 48 h after serum withdrawal, either prior to fixation (phase contrast, top row), or after fixation and staining for ISEL+, BrdU-immunofluorescence, and/or DAPI nuclear counterstaining (the DAPI and ISEL+panels represent the same field of view; the phase contrast and BrdU panels are from parallel cultures). Total cell number is greater in LPA-treated cultures, while the number of apoptotic cells detected morphologically or by ISEL+labeling is decreased. In contrast, LPA treatment does not affect BrdU incorporation. Scale bars, 30 nM. b) LPA significantly decreases apoptosis as detected by ISEL+at doses as low as 10 μM. Numbers are expressed as percent of control ISEL-labeled cell numbers. *$p<0.05$; **$p<0.0001$ (vs. control). inset, northern blot analysis of 7 μg total RNA shows that $lp_{A1}$/vzg-l expression is maintained following serum withdrawal. c) BrdU incorporation is not affected by LPA-treatment following serum withdrawal, though cells are capable of proliferation following addition of 10% fetal calf serum (FCS). *$p<0.0001$ (vs. control). d) The survival-promoting effect of LPA is also evidenced by increased maintenance of cell number following 48 h-serum withdrawal. *$p<0.0001$ (vs. control). e) The lysosphingolipid S1P does not promote SC survival, indicating a specific effect of LPA (S1P vs. control, $p>0.3$). *$p<0.0001$ (vs. control). f) LPA (1 μM) is as effective in promoting SC survivals as a maximal dose (100 ng/ml, determined in pilot experiments) of a highly active, truncated form of neuregulin (NRG [Carraway et al., *Nature* 387, 512–516 (1997)]), a proven promoter of SC survival [Syroid, et al., *PNAS USA* 93, 9229–34 (1996), Grinspan, et al., *J. Neurosci* 16, 6107–18 (1996)] LPA and NRG do not act synergistically when added together at these maximal doses, and only slightly but not significantly so at lower doses (not shown), suggesting that their signaling pathways share a common downstream effector. *$p<0.01$ (vs. control). LPA, NRG, and LPA+NRG treatments were not significantly different from each other. Data presented in a–f are means (with s.e.m. bars) of 3–5 experiments performed in duplicate. p values are from ANOVA with Fisher's PLSD post-hoc analyses.
Figure 2B:
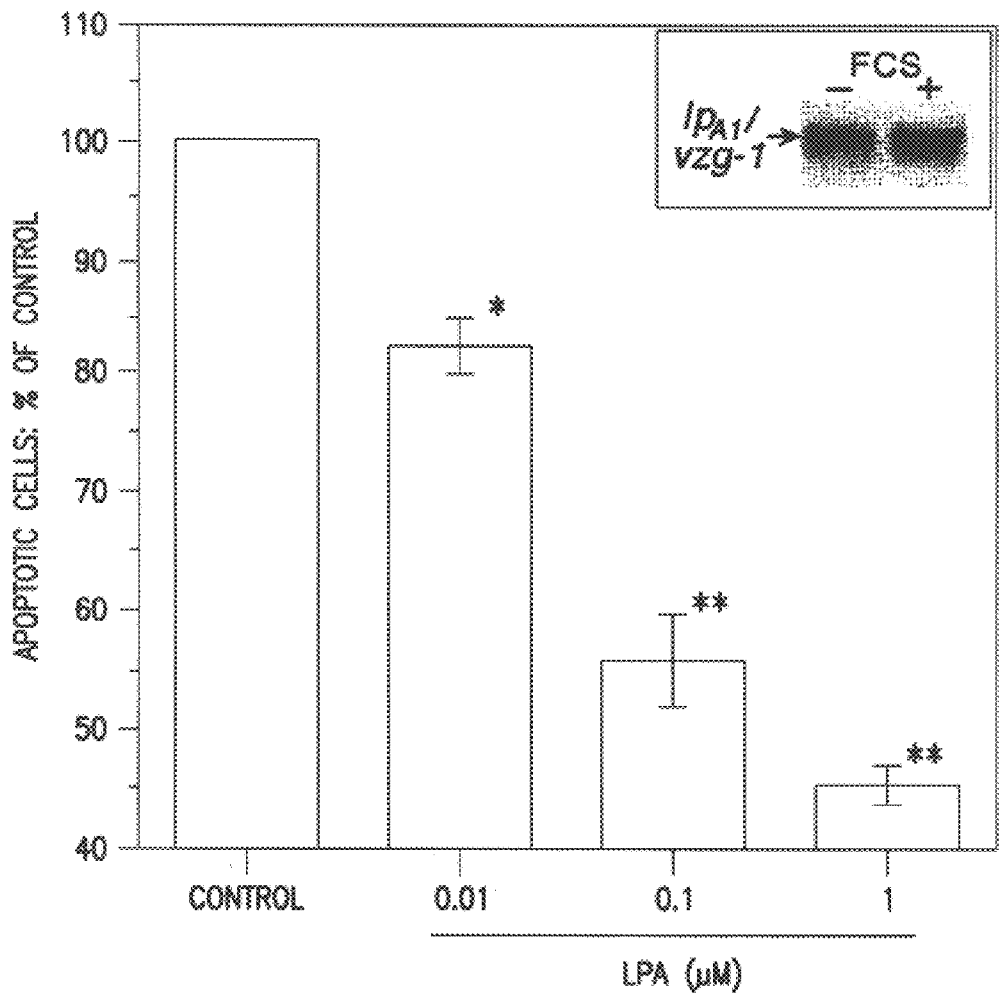
Figure 2C:
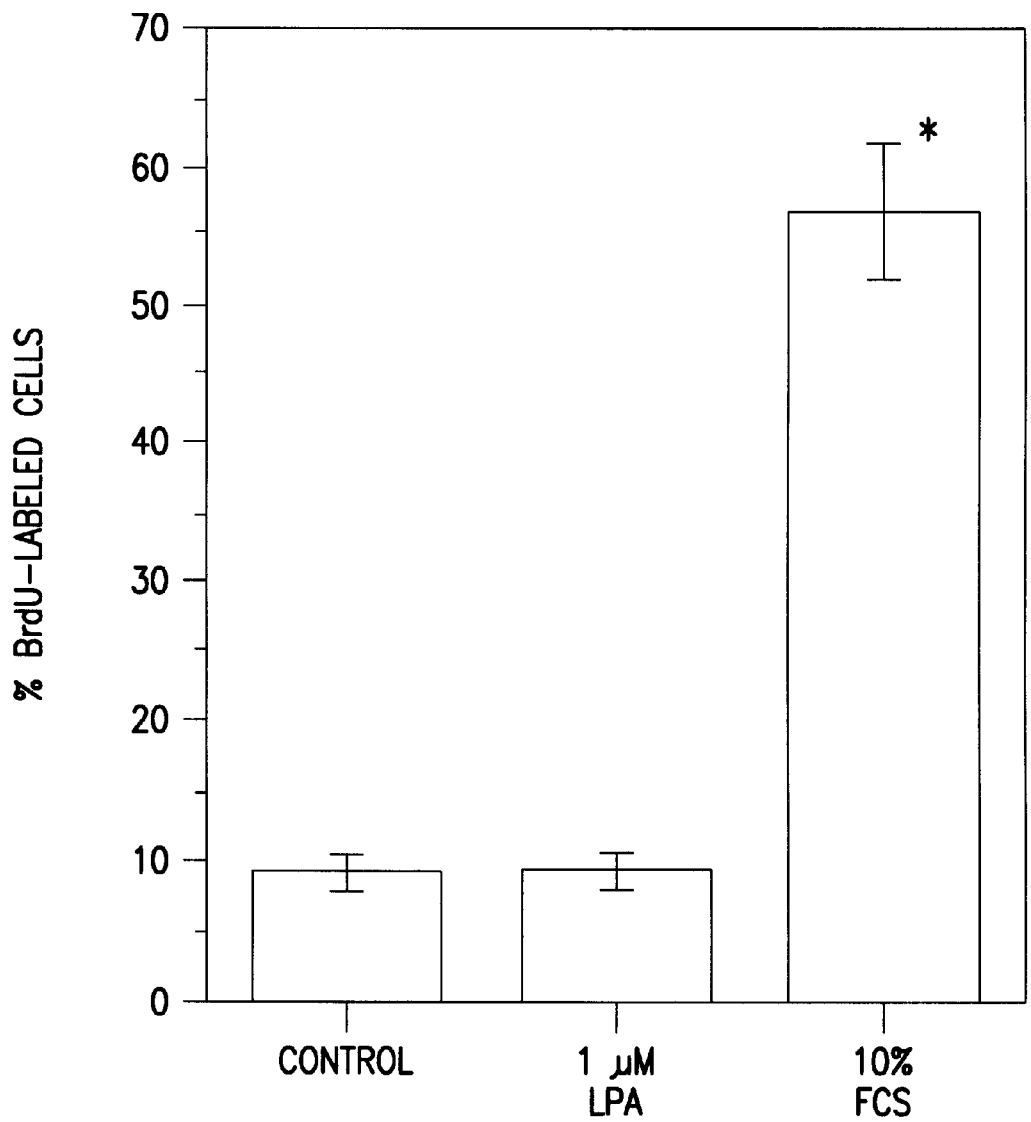

To examine the possible survival-promoting effects of LPA, apoptosis was induced by switching SCs to serum-free medium. In control cultures, cell death began soon after serum withdrawal, and by 48 h, significant cell loss was observed, with many cells exhibiting an apoptotic morphology (FIG. 2a). Treatment of SCs with LPA over 48 h led to a clear reduction (of up to 60%; see FIG. 2b) in the number of apoptotic cells, as identified both morphologically and after fixation and staining using the ISEL+(In Situ End-Labeling +) [Blaschke, A. J., et al., Development 122, 1165–1174 (1996); Blaschke, A. J., et al., J. Compar. Neuro. 396, 39–50 (1998)], a technique that labels the fragmented DNA ends that are an apoptotic hallmark [Wyllie, A. H., et al., J. Path. 142, 67–77 (1984)] (FIG. 2a). LPA significantly reduced SC apoptosis, assessed using ISEL+, at doses as low as 10 nM (FIG. 2b), suggesting the activation of a high-affinity receptor(s) such as $LP_{A1}$/VZG-1, which continues to be expressed following serum withdrawal (FIG. 2b, inset). LPA treatment did not increase the number of SCs incorporating bromodeoxy-uridine (BrdU; FIG. 2a, c), demonstrating that the dose-dependent increase in cell number in LPA-treated cultures (FIG. 2d) was due to increased cell survival, and not to proliferation.

Figure 2D:
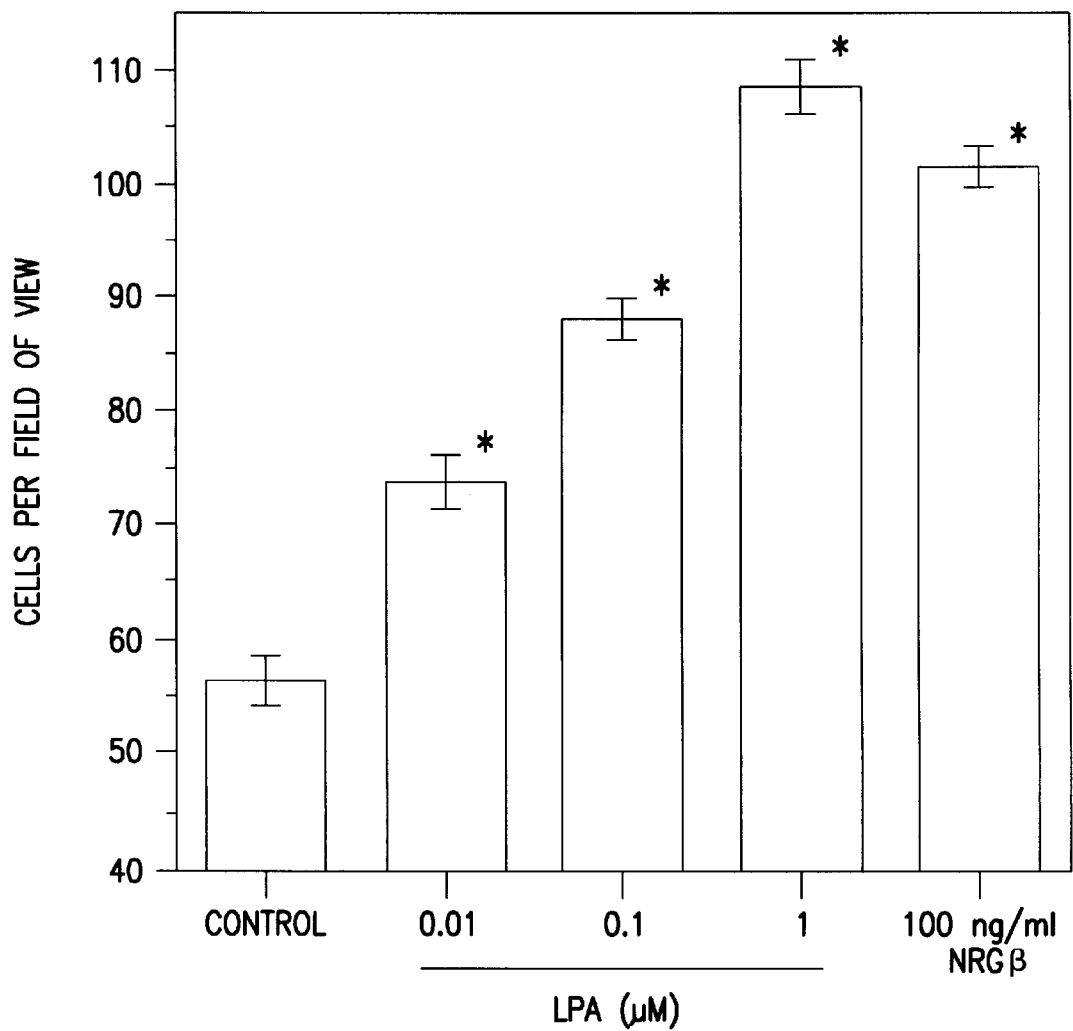
Figure 2E:
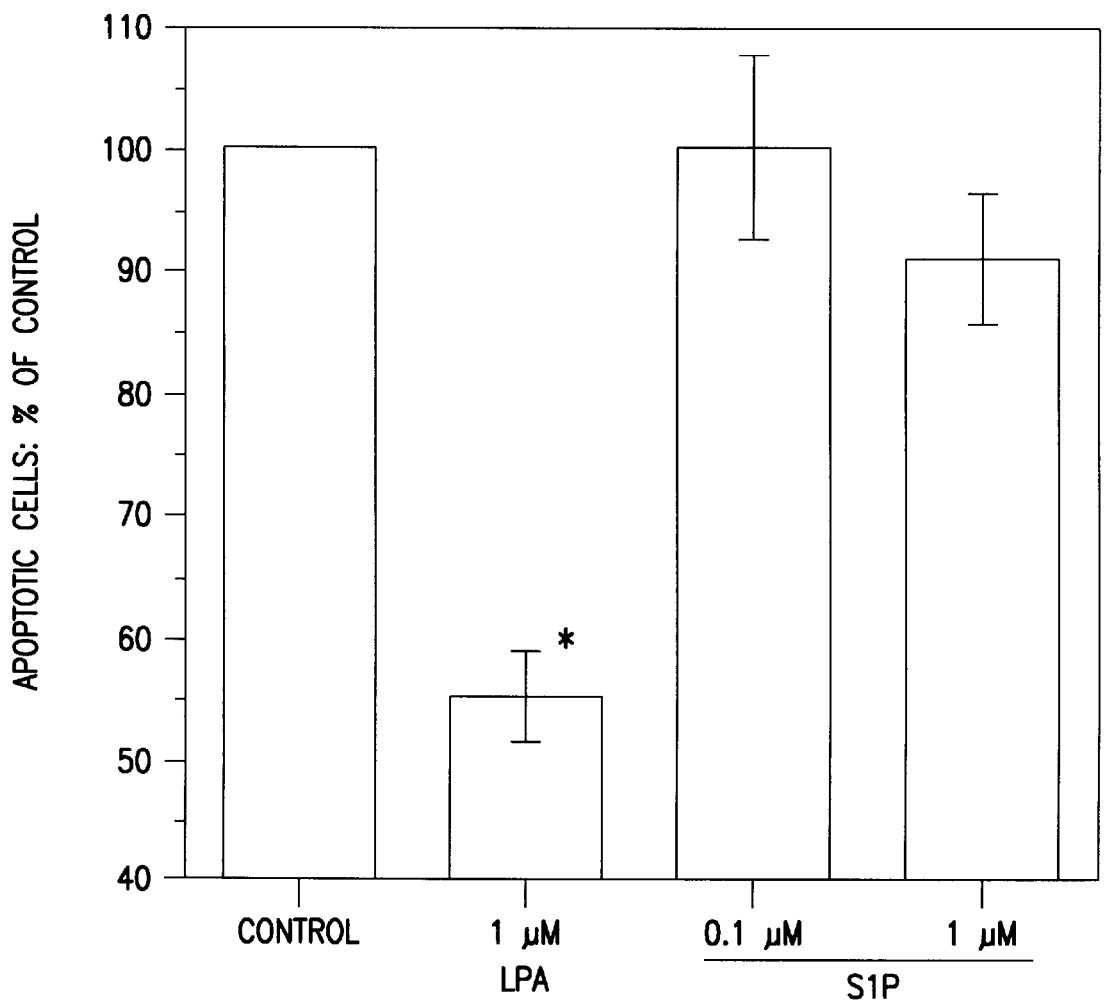

There is prominent expression of at least one of the S1P receptors [Chun, J., et al., Cell Biochem. and Biophys. in press (1998); An, S., et al., J. Biolog. Chem. 273, 7906–7910 (1998); Lee, M.-J., et al., Science in press (1998); Zondag, G. C. M., et al., Biochem. J. 330, 605–609 (1998)], LPB3 in neonatal SCs in vitro (FIG. 1). However, treatment with S1P, did not reduce SC apoptosis (FIG. 2e). These data indicate that the survival effect is LPA specific and that there are different functions for these related lipid mediators and their GPCRs in SCs.

Example 3

LPA and Neuregulins

Figure 2F:
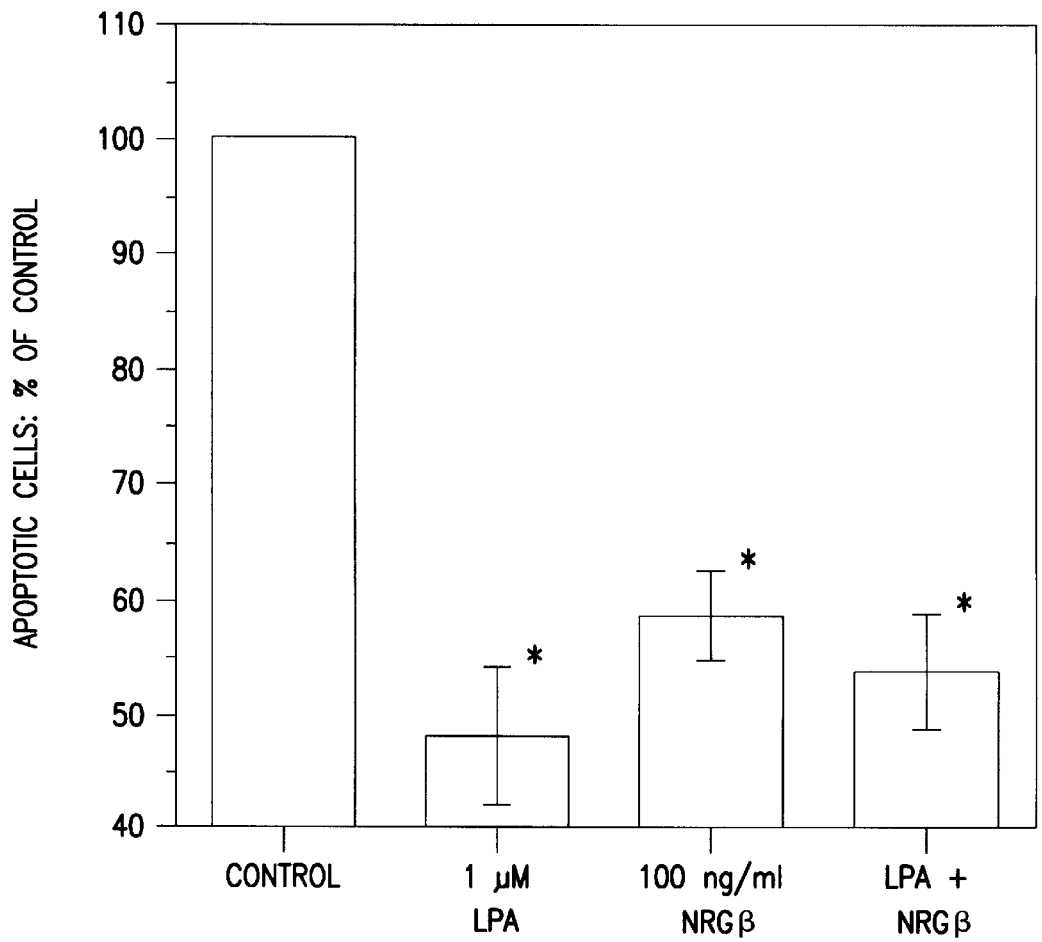

The efficacy of LPA in promoting survival was further compared to that of a family of proven SC survival factors, the neuregulins [Topilko, P., et al., *Mol. Cell Neurosci* 8, 71–75 (1996); Syroid, D. E., et al., *PNAS USA* 93, 9229–34 (1996); Grinspan, J. B., et al., *J. Neurosci.* 16, 6107–18 (1996)] {NRGs, also referred to as ARIA [Vartanian, T., et al., *PNAS USA* 91, 11620–30 (1994)], NDF [Dong, Z., et al., *Neuron* 15, 585–596 (1995)], or GGF [Lemke, G. E., et al., *J. Neurosci.* 4, 75-83 (1984)]}. A single NRG gene encodes a group of alternatively-spliced protein factors that signal through the receptor tyrosine kinases Erb 2, Erb 3, and Erb 4 [Topilko, P., et al., *Mol. Cell Neurosci* 8, 71–75 (1996)]. LPA (1 μM) was as effective in promoting SC survival as a maximal dose (100 ng/ml) of a truncated NRG β-isoform encompassing the EGF-like domain [Carraway, K. L., et al., *Nature* 387, 512–516 (1997)] that was previously shown to be highly effective in promoting survival [Syroid, D. E., et al., *PNAS USA* 93, 9229–34 (1996)] (FIG. 2*d, f*). LPA and NRG β did not have a significantly synergistic effect when added together at maximal (FIG. 2*f*) of half-maximal (not shown) doses, suggesting that their distinct receptors and signaling pathways may converge on common downstream effectors.

Although the lipid nature of LPA makes it experimentally difficult to assess whether it is produced by peripheral nerve axons, as are NRGs [Topilko, P., et al., *Mol. Cell Neurosci.* 8, 71–75 (1996)], like the NRGs, LPA can exist in both membrane-bound and soluble forms. LPA may be released by SCs themselves as an autocrine product of lipid metabolism during the elaboration of the myelin sheath, which is about 80% lipid, including complex phospholipids [Gould, R. M., et al., *Bio. Chem*, 123–171 (CRC Press, Boca Raton, 1992]. Moreover as LPA is released by activated platelets [Eichholtz, T., et al., *Biochem. J.* 291, 677–680 (1993)], it is likely to be present following peripheral nerve injury, where it could influence regeneration by promoting the survival of SCs.

Example 4

LPA Receptor Activation

Figure 3A:
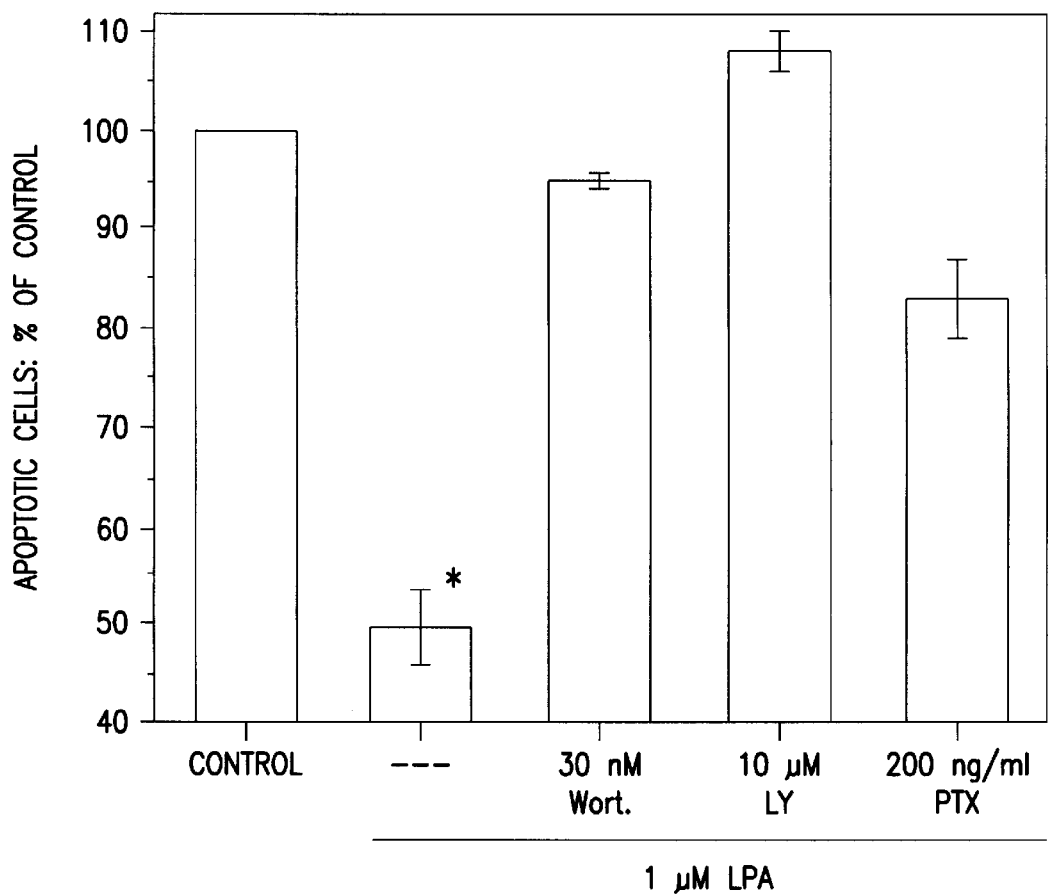
FIG. 3. Promotion of SC survival by LPA involves $G_1$ and the P13K/Akt pathway. a) promotion of SC survival by LPA ("———" lane) is significantly reduced by pretreatment of cells with pertussis toxin (PTX), indicating the involvement of $G_1$ and is completely blocked by wortmannin (Wort.) and LY294002 (LY), indicating its dependence on P13K. Data presented are means (with s.e.m. bars) of 3–4 experiments performed in duplicate. *$p<0.0001$ (vs. control), by t-test with matched control. All other means were not significantly different from their matched controls (i.e. pharmacological inhibitor alone; p values between 0.1 and 0.6). b) c) western blots probed with antibodies specific for the Ser473-phosphorylated form of Akt (-phosoho-Akt), with parallel loading control blots probed with antibodies detecting all Akt (-Akt). Treatment of SCs with LPA (1 μM) induces a transient (<lb, b) increase in Akt phosphorylation at site (Ser473) required for its activation [Franke et al., *Cell* 88, 435–437 (1997)]. This LPA-induced increase in Akt phosphorylation is blocked by pretreatment of SCs with Wort, or LY, but not with the MAP kinase pathway inhibitor PD98059 (PD, c), consistent with data showing that P13K activation is upstream of Akt activation kDa, kilodaltons.

Prevention of SC apoptosis by LPA was inhibited by pretreatment of SCs with pertussis toxin (PTX; FIG. 3*a*), indicating the involvement of $G_i$ to which $LP_{A1}$/VZG-1/Edg 2 has been demonstrated to couple directly [Fukushima, N., et al., *PNAS USA* in press (1998)]. Accordingly, the activation of the LPA receptors, including LPA$_1$/VZG-1/Edg 2, are believed to be directly involved in the promotion of SC survival.

Example 5

LPA and the P13K/AKT Pathway

Figure 3B:
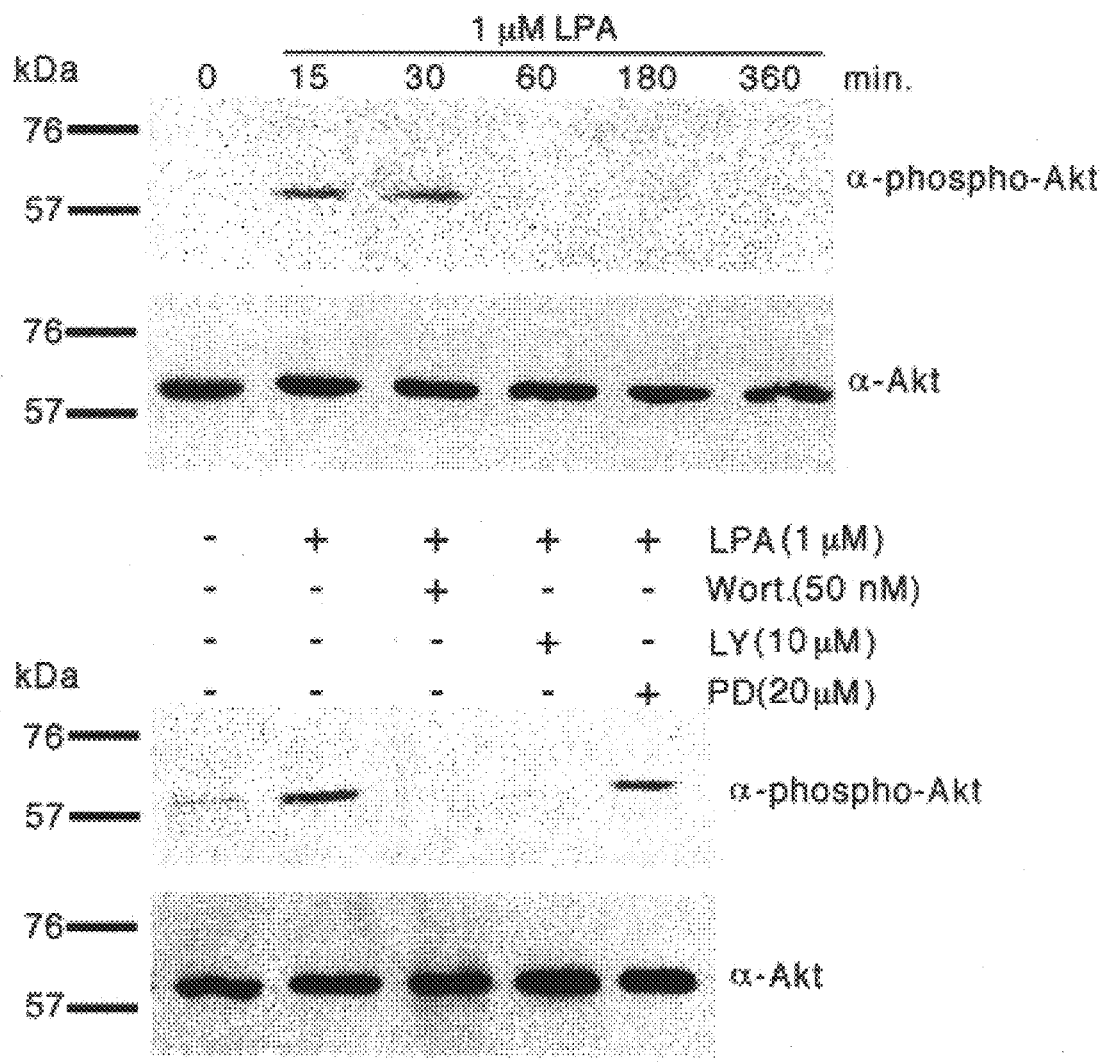

LPA-dependent survival was blocked completely by two P13K inhibitors, wortmannin and LY 294002 (FIG. 3*a*). Sequential activation of P13K and the serine-threonine kinase Akt (PKB) has been linked to the prevention of apoptosis in various cell types through phosphorylation of BAD, a pro-cell death member of the Bcl-2 family. As NRG can also activate a P13K pathway these data could explain the lack of a synergistic survival effect of LPA and NRG β (see above, FIG. 2*f*). Addition of 1 μM LPA to SCs in serum-free medium induced a rapid and transient increase in the phosphorylation of Akt at a site (Ser473) required for its activation [Franke, T. F., et al., *Cell* 88, 435–437 (1997)], as detected by western blot analysis (FIG. 3*b*). This accumulation of phospho-Akt in response to LPA was dependent on P13K, as it was blocked by both wortmannin and LY294002, but not by the MAP kinase pathway inhibitor PD98059 (FIG. 3*c*). These data identify LPA as a novel activator of the P13K/Akt pathway, and implicate the activity of this pathway in promoting SC survival.

EXAMPLE 6

Overexpression of $LP_{A1}$ Recptor

Figure 4A:
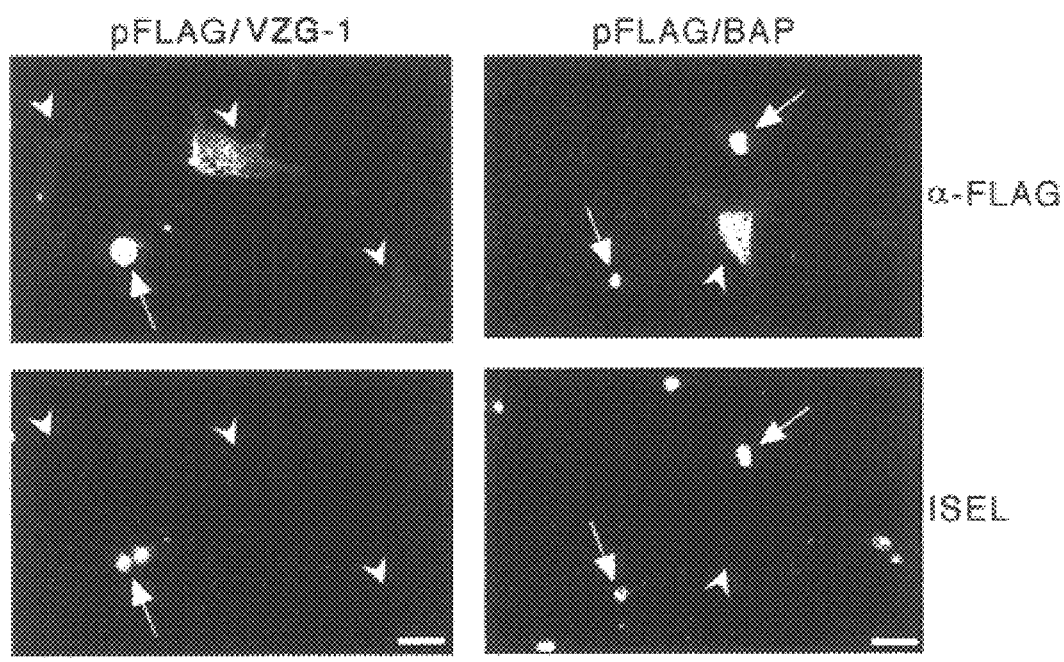
FIG. 4. Overexpression of the LPA receptor $LP_{A1}$/VZG-l potentiates SC survival. a) photomicrographs of SCs transfected with pFLAG/VZG-l (encoding a FLAG-epitope tagged $LP_{A1}$/VZG-l receptor) or with pFLAG/BAP (encoding a FLAG-epitope tagged bacterial alkaline phosphatase control protein), double-labeled for -FLAG immunofluorescence (red) and a fluorescent ISEL technique (green) to detect apoptotic cells. Double-labeled, apototic transfected cells (arrows), as well as healthy transfected cells (arrowheads), are clearly identifiable. Scale bars, 30 μM. b) overexpression of epitope tagged $LP_{A1}$/VZG-l significantly potentiates SC survival (vs. transfection control) both with and without a sub-maximal (0.1 μM) dose of LPA. The effect of 1 μM LPA was also potentiated, but this failed to reach significance ($p=0.19$). Data (% apoptotic transfected cells) are presented as means (with s.e.m. bars) of 3 experiments performed in triplicate. *$p<0.005$ (vs. matched pFLAG/BAP transfection control condition) by ANOVA (significant main effects of LPA treatment and plasmid transfection conditions) and Fisher's PLSD post-hoc analyses.
Figure 4B:
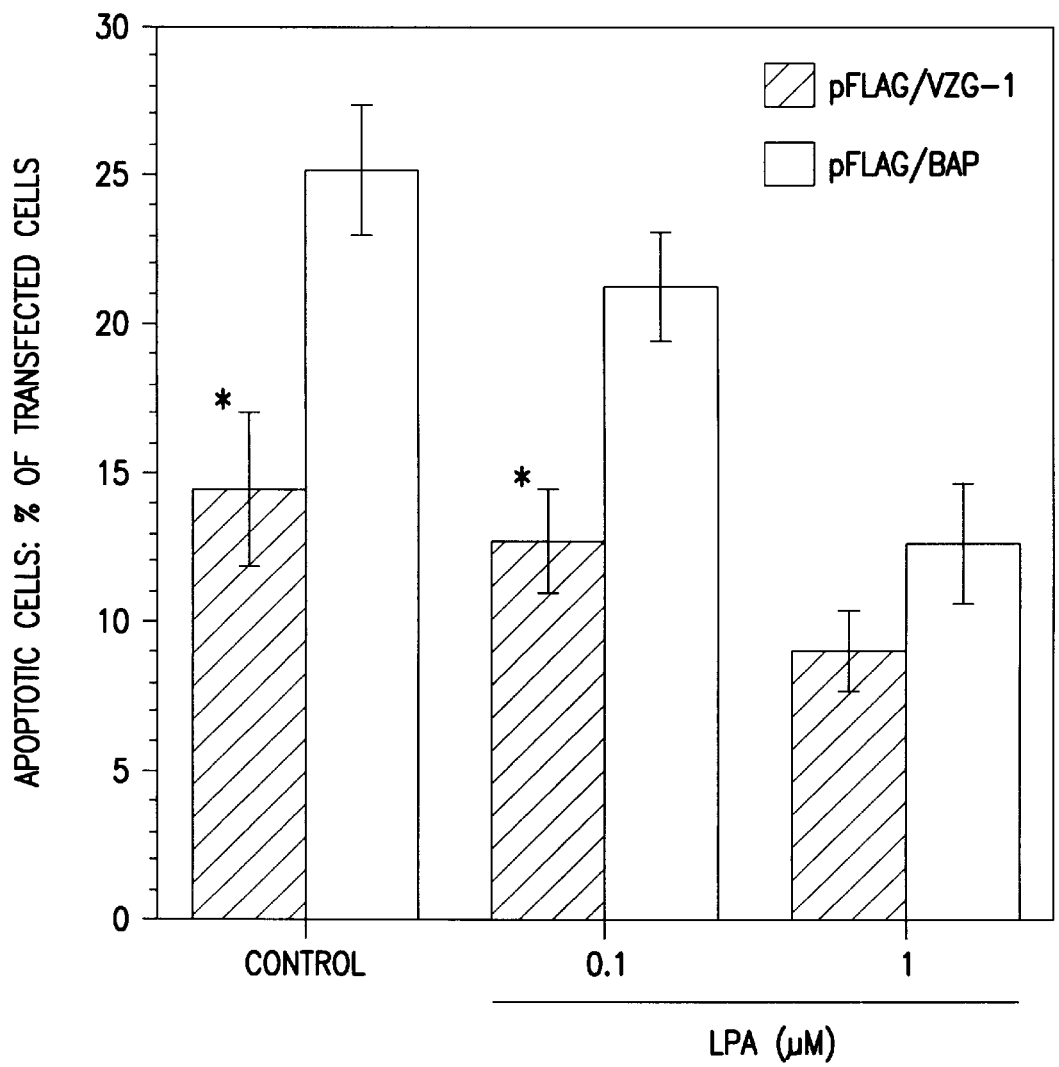

The prominent expression of lp$_{A1}$/vzg-1 in the absence of another reported LPA receptor gene [An, S., et al., *FEBS Letters* in press (1998); Chun, J., et al., *Cell Biochem. and Biophys.* in press (1998)](FIG. 1), along with the effectiveness of LPA at low nanomolar doses indicates that this high affinity receptor mediates LPA-dependent SC survival. In addition, FLAG epitope-tagged $LP_{A1}$/VZG-1 was overexpressed by transfection with an expression construct to determine if this receptor did mediate LPA-dependent SC survival. After overexpressing FLAG epitope-tagged $LP_{A1}$/VZG-1 by transfecting with an expression vector and withdrawing the serum, the apoptotic transfected cells were identified 24 h later by double labeling for anti-FLAG immunofluorescence and fluorescent ISEL (FIG. 4*a*). Overexpression of epitope-tagged $LP_{A1}$/VZG-1 significantly potentiated SC survival in serum-free medium (compared to transfection with a FLAG-tagged bacterial alkaline phosphatase (BAP) control construct), both with and without a sub maximal (0.1 μM) dose of LPA (FIG. 4*b*). $LP_{A1}$/VZG-1 overexpression also modestly potentiated the effect of 1 μM LPA (FIG. 4*b*); the smaller effect likely reflects maximal activation of endogenous receptors at this dose. The increase in survival of $LP_{A1}$/VZG-1 transfected cells even in the absence of added LPA may reflect basal receptor coupling activity, which has been observed with overexpression of GPCRs [Milano, C. A., et al., *Science* 264, 582–586 (1994); Fukushima, N., et al., *PNAS USA* in press (1998)], and/or residual effects of serum-derived LPA present in the media prior to 24 h serum withdrawal (see Methods). These results, together with the LPA potency and expression data noted above, indicates that prevention of SC apoptosis by LPA can be mediated by the high affinity LPA receptor $LP_{A1}$/VZG-1.

It will be well understood by a skilled person in the art that the invention as herein described and exemplified may be modified without departing from the scope of the invention as defined in the claims appended hereto.

We claim:

1. A method for promoting survival of myelin producing cells comprising treating myelin producing cells with an effective amount of lysophosphatidic acid (LPA) to promote cell survival.

2. The method according to claim 1, wherein the myelin producing cells are oligodendrocytes.

3. The method according to claim 1, wherein the myelin producing cells are Schwann cells.

4. The method according to claim 3, wherein LPA is an agonist to a $LP_{A1}$/VZG-1/edg-2 receptor.

5. The method according to claim 3, wherein the Schwann cells are treated in vitro or ex vivo.

6. The method according to claim 5, comprising the step of culturing the Schwann cell in a serum-free culture growth medium comprising LPA, and suitable cell culture excipients.

7. The method according to claim 6 wherein LPA is an agonist to a $LP_{A1}$/VZG-1/edg-2 receptor.

8. A method for enhancing the development or regeneration of myelin by promoting the survival of myelin producing cells comprising treating myelin producing cells with an effective amount of LPA to promote cell survival.

9. The method according to claim 8, wherein the myelin producing cells are oligodendrocytes.

10. The method according to claim 9, wherein the myelin producing cells are Schwann cells.

11. The method according to claim 10, wherein LPA is an agonist to a $LP_{A1}$/VZG-l/edg-2 receptor.

12. A method of promoting survival of endogenous myelin producing cells in a subject, comprising delivering to the subject an effective amount of LPA.

13. The method according to claim 12, wherein the endogenous myelin producing cells are endogenous Schwann cells.

14. The method according to claim 12, wherein the endogenous myelin producing cells are endogenous oligodendrocytes.

15. A method of treating a subject with a neurological disorder related to the loss of myelination comprising delivering to the subject an effective amount of LPA.

16. The method according to claim 15, wherein said neurological disorder is Multiple Sclerosis.

* * * * *

UNITED STATES PATENT AND TRADEMARK OFFICE
CERTIFICATE OF CORRECTION

PATENT NO. : 6,150,345
DATED : November 21, 2000
INVENTOR(S) : Chun et al.

It is certified that error appears in the above-identified patent and that said Letters Patent is hereby corrected as shown below:

Column 13,
Line 3, delete "claim 9" and insert -- claim 8 --, therefor.

Signed and Sealed this

Ninth Day of October, 2001

Attest:

NICHOLAS P. GODICI
Attesting Officer
Acting Director of the United States Patent and Trademark Office